United States Patent
Milne et al.

(10) Patent No.: US 12,425,783 B2
(45) Date of Patent: Sep. 23, 2025

(54) PRE-MADE PROFILES FOR AUDITORY DEVICES

(71) Applicant: Sony Group Corporation, Tokyo (JP)

(72) Inventors: James R. Milne, Romona, CA (US); Allison Burgueno, Oceanside, CA (US); Justin Kenefick, San Diego, CA (US); Gregory Carlsson, Santee, CA (US)

(73) Assignee: SONY GROUP CORPORATION, Tokyo (JP)

( * ) Notice: Subject to any disclaimer, the term of this patent is extended or adjusted under 35 U.S.C. 154(b) by 212 days.

(21) Appl. No.: 18/240,267

(22) Filed: Aug. 30, 2023

(65) Prior Publication Data

US 2025/0080930 A1      Mar. 6, 2025

(51) Int. Cl.
*H04R 25/00*      (2006.01)
(52) U.S. Cl.
CPC .......... *H04R 25/558* (2013.01); *H04R 25/50* (2013.01); *H04R 25/70* (2013.01)
(58) Field of Classification Search
CPC ...... H04R 25/558; H04R 25/50; H04R 25/70; H04R 1/1041; H04R 2225/55; H04R 25/507; A61B 5/123
See application file for complete search history.

(56) References Cited

U.S. PATENT DOCUMENTS

| | | | |
|---|---|---|---|
| 9,468,401 B2 | 10/2016 | Van Hasselt | |
| 10,595,135 B2 | 3/2020 | Li | |
| 2014/0194775 A1 | 7/2014 | Van Hasselt | |
| 2022/0021986 A1 | 1/2022 | Beck | |

FOREIGN PATENT DOCUMENTS

IN          202021053345          10/2022

*Primary Examiner* — Tuan D Nguyen
(74) *Attorney, Agent, or Firm* — Trellis IP Law Group, PC (57) ABSTRACT

A computer-implemented method includes downloading a hearing application. The method further includes providing a user interface that includes an option for a user associated with the user device to take a hearing test. The method further includes responsive to receiving a rejection of the option to take the hearing test, updating the user interface to include a list of user preferences. The method further includes receiving one or more user preferences from the user. The method further includes updating the user interface to include a set of profiles based on the one or more user preferences. The method further includes receiving a selection of a profile from the set of profiles. The method further includes instructing an auditory device to implement the selected profile.

20 Claims, 8 Drawing Sheets

PRE-MADE PROFILES FOR AUDITORY DEVICES

BACKGROUND

Hearing aids and other auditory devices are used to block out certain noises and amplify others. The first step is typically to perform a hearing test to determine a user's inability to hear certain frequencies. However, when a hearing test is performed by an audiologist, the test may take hours. When the hearing test is performed by an application, the test may still take too long for a user and the user may not complete the test and use their hearing aids.

SUMMARY

In some embodiments, a computer-implemented method includes downloading, with a user device, a hearing application. The method further includes providing a user interface that includes an option for a user associated with the user device to take a hearing test. The method further includes responsive to receiving a rejection of the option to take the hearing test, updating the user interface to include a list of user preferences. The method further includes receiving one or more user preferences from the user. The method further includes updating the user interface to include a set of profiles based on the one or more user preferences. The method further includes receiving a selection of a profile from the set of profiles. The method further includes instructing an auditory device to implement the selected profile.

In some embodiments, the user preferences include an identification of demographic information for the user and the set of profiles includes a demographic-based profile. In some embodiments, the user preferences include an identification of a hearing condition and the set of profiles includes a hearing-condition based profile. In some embodiments, the set of profiles includes one or more popular profiles. In some embodiments, the method further includes providing an option to rate the selected profile, scoring the selected profile based on a rating from the user, and updating the one or more popular profiles based on the score associated with the selected profile. In some embodiments, the set of profiles includes an audiologist-designed profile. In some embodiments, the method further includes providing user preferences as input to a machine-learning model and outputting, with the machine-learning model, a machine-learning profile. In some embodiments, the method further includes updating the user interface to include a set of presets. In some embodiments, the method further includes receiving a selection of the option to create a new preset for a current location; sampling a background noise for a period of time; and outputting, with a machine-learning model, the new preset for an ambient noise condition that modifies adjustments in sound levels based on patterns associated with the ambient noise condition.

In some embodiments, a user device includes one or more processors and logic encoded in one or more non-transitory media for execution by the one or more processors and when executed are operable to: receive a trained machine-learning model; provide a user interface that includes an option for a user associated with the user device to take a hearing test; responsive to receiving a rejection of the option to take the hearing test, update the user interface to include a list of user preferences; receive one or more user preferences from the user; provide the one or more user preferences as input to the trained machine-learning model; output, with the trained machine-learning model, a machine-learning profile; and instruct an auditory device to implement the machine-learning profile.

In some embodiments, the logic is further operable to: update the user interface to include a set of profiles based on the one or more user preferences, receive a selection of a profile from the set of profiles, and instruct an auditory device to implement the selected profile. In some embodiments, the user preferences include an identification of a hearing condition and the set of profiles includes a hearing-condition based profile. In some embodiments, the user preferences include an identification of a hearing condition and the set of profiles includes a hearing-condition based profile. In some embodiments, the set of profiles includes one or more popular profiles. In some embodiments, the logic is further operable to: provide an option to rate the selected profile, score the selected profile based on a rating from the user, and update the one or more popular profiles based on the score associated with the selected profile.

Software encoded in one or more computer-readable media for execution by the one or more processors of an auditory device and when executed is operable to: download, with a user device, a hearing application; provide a user interface that includes an option for a user associated with the user device to take a hearing test; responsive to receiving a rejection of the option to take the hearing test, update the user interface to include a list of user preferences; receive one or more user preferences from the user; update the user interface to include a set of profiles based on the one or more user preferences; receive a selection of a profile from the set of profiles; and instruct an auditory device to implement the selected profile.

In some embodiments, the user preferences include an identification of demographic information for the user and the set of profiles includes a demographic-based profile. In some embodiments, the user preferences include an identification of a hearing condition and the set of profiles includes a hearing-condition based profile. In some embodiments, the set of profiles includes one or more popular profiles. In some embodiments, the software is further operable to: provide an option to rate the selected profile, score the selected profile based on a rating from the user, and update the one or more popular profiles based on the score associated with the selected profile.

The technology advantageously provides a set of profiles that are customized for a user. For example, a user may be able to select a profile for female users over 60, where the profile will help the user with hearing difficulties without having to take a hearing test.

A further understanding of the nature and the advantages of particular embodiments disclosed herein may be realized by reference of the remaining portions of the specification and the attached drawings.

DETAILED DESCRIPTION OF EMBODIMENTS

Example Environment 100

Figure 1:
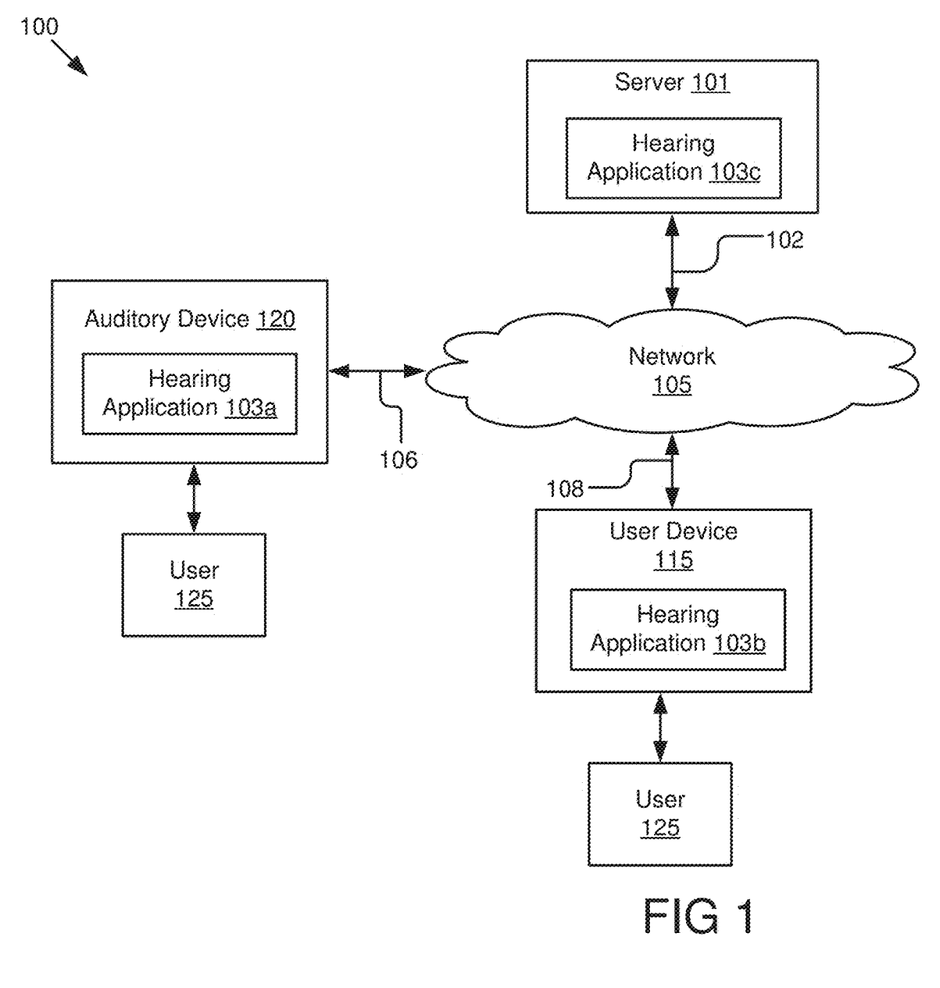
FIG. 1 is a block diagram of an example network environment according to some embodiments described herein.

FIG. 1 illustrates a block diagram of an example environment 100. In some embodiments, the environment 100 includes an auditory device 120, a user device 115, and a server 101. A user 125 may be associated with the user device 115 and the auditory device 120. In some embodiments, the environment 100 may include other servers or devices not shown in FIG. 1. In FIG. 1 and the remaining figures, a letter after a reference number, e.g., "103a," represents a reference to the element having that particular reference number (e.g., a hearing application 103a stored on the user device 115). A reference number in the text without a following letter, e.g., "103," represents a general reference to embodiments of the element bearing that reference number (e.g., any hearing application 103).

The auditory device 120 may include a processor, a memory, a speaker, and network communication hardware. The auditory device 120 may be a hearing aid, earbuds, headphones, or a speaker device. The speaker device may include a standalone speaker, such as a soundbar or a speaker that is part of a device, such as a speaker in a laptop, tablet, phone, etc.

The auditory device 120 is communicatively coupled to the network 105 via signal line 106. Signal line 106 may be a wired connection, such as Ethernet, coaxial cable, fiber-optic cable, etc., or a wireless connection, such as Wi-Fi®, Bluetooth®, or other wireless technology.

In some embodiments, the auditory device 120 includes a hearing application 103a that receives instructions from a hearing application 103b stored on the user device 115. In some embodiments, the hearing application 103a performs hearing tests. For example, the user 125 may be asked to identify sounds emitted by speakers of the auditory device 120 and the user may provide user input, for example, by pressing a button on the auditory device 120, such as when the auditory device is a hearing aid, earbuds, or headphones. In some embodiments where the user 125 does not want to take a hearing test, the hearing application 103a receives instructions from the hearing application 103b to implement a hearing profile. The hearing application 103a may additionally receive instructions to implement a preset.

The user device 115 may be a computing device that includes a memory, a hardware processor, and a hearing application 103b. The user device 115 may include a mobile device, a tablet computer, a laptop, a mobile telephone, a wearable device, a head-mounted display, a mobile email device, or another electronic device capable of accessing a network 105 to communicate with one or more of the server 101 and the auditory device 120.

In the illustrated implementation, user device 115 is coupled to the network 105 via signal line 108. Signal line 108 may be a wired connection, such as Ethernet, coaxial cable, fiber-optic cable, etc., or a wireless connection, such as Wi-Fi®, Bluetooth®, or other wireless technology. The user device 115 is used by way of example. While FIG. 1 illustrates one user device 115, the disclosure applies to a system architecture having one or more user devices 115.

In some embodiments, the hearing application 103b includes code and routines operable to provide a user interface that includes an option for a user associated with the user device to take a hearing test. Responsive to receiving a rejection of the option to take the hearing test, the hearing application 103b may update the user interface to include a list of user preferences. The hearing application 103b may receive one or more user preferences from the user and update the user interface to include a set of profiles based on the user preferences. The hearing application 103b may receive a selection of a profile from the set of profiles. The hearing application 103b may instruct the auditory device 120 to implement the selected profile.

The server 101 may include a processor, a memory, and network communication hardware. In some embodiments, the server 101 is a hardware server. The server 101 is communicatively coupled to the network 105 via signal line 102. Signal line 102 may be a wired connection, such as Ethernet, coaxial cable, fiber-optic cable, etc., or a wireless connection, such as Wi-Fi®, Bluetooth®, or other wireless technology. In some embodiments, the server includes a hearing application 103c. In some embodiments and with user consent, the hearing application 103c on the server 101 maintains a copy of a user profile, where the user profile includes one or more of a selected profile, a preset, and a hearing profile. In some embodiments, the server 101 maintains audiometric profiles generated by an audiologist for different situations, such as an audiometric profile of a person with no hearing loss, an audiometric profile of a man with no hearing loss, an audiometric profile of a woman with hearing loss, etc. In some embodiments, the hearing application 103c on the server 101 includes a trained machine-learning model and provides information to the auditory device 120 and/or the user device 115 about a machine-learning profile and a machine-learning preset in order to take advantage of greater processing power provided by the server 101.

Figure 2:
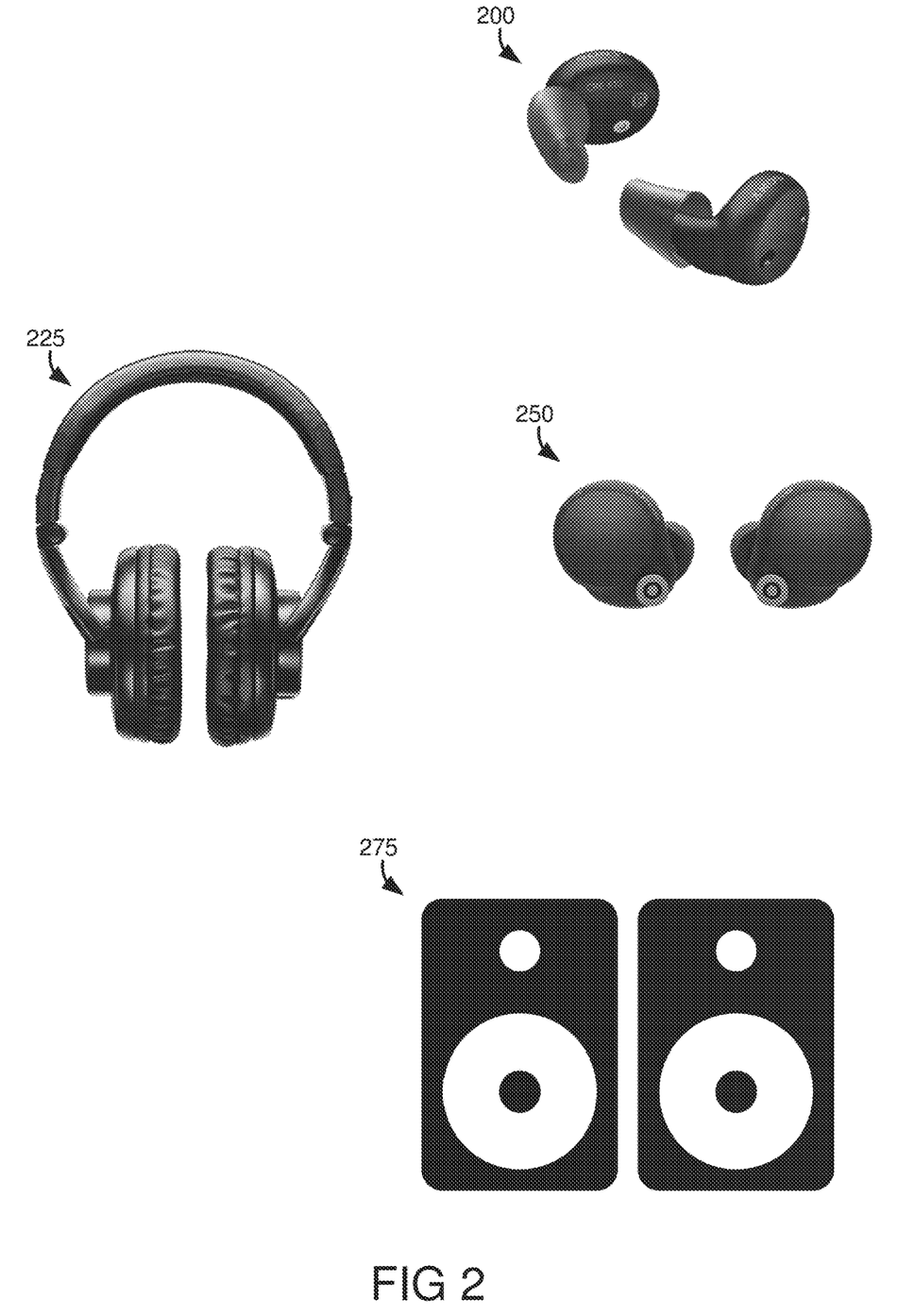
FIG. 2 is an illustration of example auditory devices according to some embodiments described herein.

FIG. 2 illustrates example auditory devices. Specifically, FIG. 2 illustrates a hearing aid 200, headphones 225, earbuds 250, and a speaker device 275. In some embodiments, each of the auditory devices is operable to receive instructions from the hearing application 103 to apply the one or more presets.

Example Computing Device 300

Figure 3A:
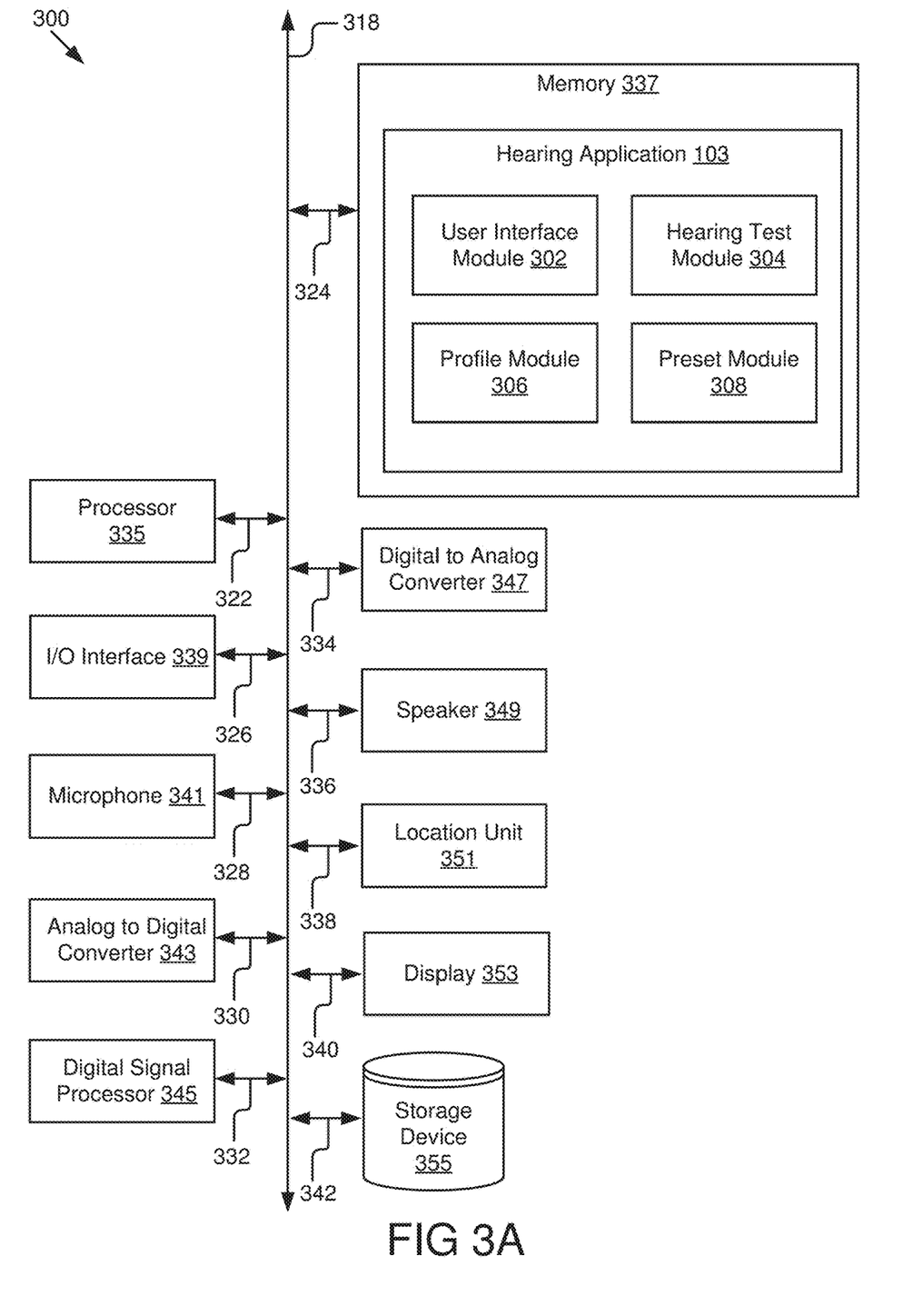
FIG. 3A is a block diagram of an example auditory device according to some embodiments described herein.

FIG. 3A is a block diagram of an example computing device 300 that may be used to implement one or more features described herein. The computing device 300 can be any suitable computer system or other electronic or hardware device. In some embodiments, the computer device 300 is the user device 115 in FIG. 1. In some embodiments, some portions of the computing device 300 are performed by the auditory device 120 and some portions of the computing device 300 are performed by the user device 115 in FIG. 1.

In some embodiments, computing device 300 includes a processor 335, a memory 337, an Input/Output (I/O) interface 339, a microphone 341, an analog to digital converter 343, a digital signal processor 345, a digital to analog converter 347, a speaker 349, a location unit 351, a display 353, and a storage device 355. The processor 335 may be coupled to a bus 318 via signal line 322, the memory 337 may be coupled to the bus 318 via signal line 324, the I/O interface 339 may be coupled to the bus 318 via signal line 326, the microphone 341 may be coupled to the bus 318 via signal line 328, the analog to digital converter 343 may be coupled to the bus 318 via signal line 330, the digital signal processor 345 may be coupled to the bus 318 via signal line 332, the digital to analog converter 347 may be coupled to the bus 318 via signal line 334, the speaker 349 may be coupled to the bus 318 via signal line 336, the location unit 351 may be coupled to the bus 318 via signal line 338, the display 353 may be coupled to the bus 318 via signal line 340, and the storage device 355 may be coupled to the bus 318 via signal line 342.

The processor 335 can be one or more processors and/or processing circuits to execute program code and control basic operations of the computing device 300. A processor includes any suitable hardware system, mechanism or component that processes data, signals or other information. A processor may include a system with a general-purpose central processing unit (CPU) with one or more cores (e.g., in a single-core, dual-core, or multi-core configuration), multiple processing units (e.g., in a multiprocessor configuration), a graphics processing unit (GPU), a field-programmable gate array (FPGA), an application-specific integrated circuit (ASIC), a complex programmable logic device (CPLD), dedicated circuitry for achieving functionality, or other systems. A computer may be any processor in communication with a memory.

The memory 337 is typically provided in computing device 300 for access by the processor 335 and may be any suitable processor-readable storage medium, such as random access memory (RAM), read-only memory (ROM), Electrical Erasable Read-only Memory (EEPROM), Flash memory, etc., suitable for storing instructions for execution by the processor or sets of processors, and located separate from processor 335 and/or integrated therewith. Memory 337 can store software operating on the computing device 300 by the processor 335, including the hearing application 103.

The I/O interface 339 can provide functions to enable interfacing the computing device 300 with other systems and devices. Interfaced devices can be included as part of the computing device 300 or can be separate and communicate with the computing device 300. For example, network communication devices, storage devices (e.g., the memory 337 or the storage device 355), and input/output devices can communicate via I/O interface 339.

In some embodiments, the I/O interface 339 handles communication between the computing device 300 and the user device via a wireless protocol, such as Wi-Fi®, Bluetooth®, Near Field Communication (NFC), Radio Frequency Identification (RFID), Ultra-Wideband (UWB), infrared, etc. In some embodiments, the I/O interface 339 provides information to the user device that identifies a type of the auditory device that is wirelessly connected to the user device.

The microphone 341 includes hardware for detecting sounds. For example, the microphone 341 may detect ambient noises, people speaking, music, etc. The microphone 341 receives acoustical sound signals and converts the signals to analog electrical signals. The analog to digital converter 343 converts the analog electrical signals to digital electrical signals.

Figure 3B:
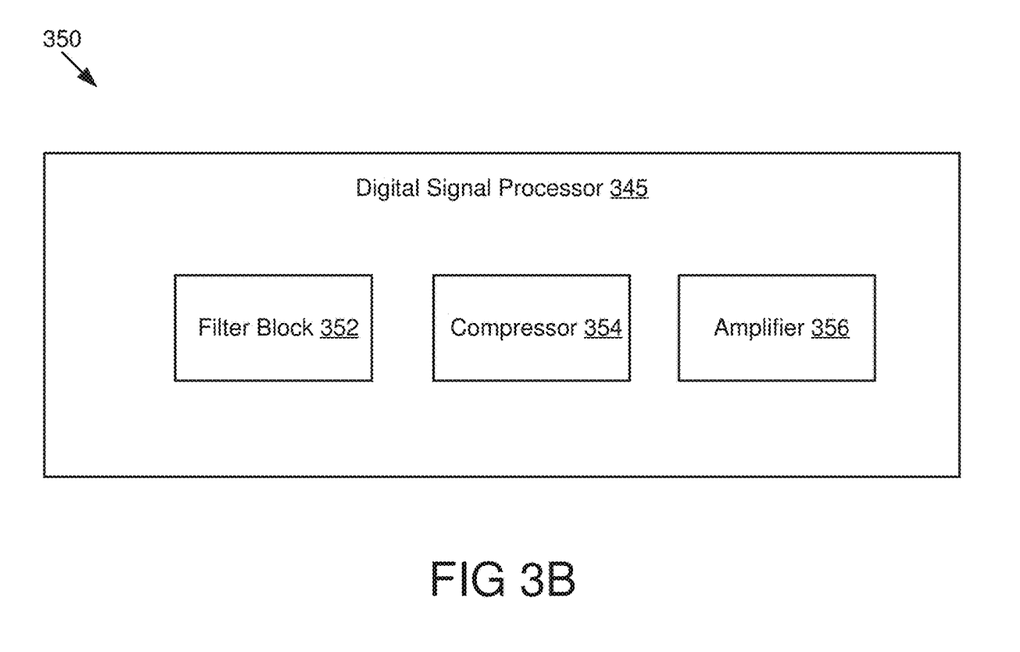
FIG. 3B is a block diagram of an example digital signal processor according to some embodiments described herein.

The digital signal processor 345 includes hardware for converting the digital electrical signals into a digital output signal. Turning to FIG. 3B, an example digital signal processor 345 is illustrated. In some embodiments, the digital signal processor 345 includes a filter block 352, a compressor 354, and an amplifier 356.

The filter block 352 includes hardware that may apply a filter to the digital electrical signals. For example, the filter block 352 may apply a filter that removes sounds corresponding to a particular frequency or that modifies the sound level associated with the particular frequency. For example, the filter block 352 may include a high-frequency shelf that prevents a sound level of the background noise from exceeding a high-frequency protection preset curve based on a frequency of the background noise.

The compressor 354 may include hardware that is used to compress the dynamic range of input sounds so that they more closely match the dynamic range desired by the user while ensuring that the sounds are audible to the user. In some embodiments, the compressor 354 adjusts the gain of signals at a particular frequency where the user has hearing loss. For example, if a user has hearing loss at a higher frequency, the compressor 354 may adjust the gain of those signals.

The amplifier 346 is used to amplify certain sounds based on a particular setting. For example, the amplifier 346 may apply a gain to particular frequencies when a user has been identified as suffering hearing loss at those particular frequencies. In some embodiments, the amplifier 346 reduces or blocks a signal heard by the user by sending an inverted signal that sums with the outside noise before it reaches the user's ear. The amplifier 346 transmits the digital output signal to a digital-to-analog converter 347.

The digital-to-analog converter 347 may include hardware that is used to convert the digital output signal into an analog electrical signal, which is used by the speaker 349 to produce an audio signal that is heard by the user.

The location unit 351 includes hardware to identify a current location of the computing device 300. The location unit 351 includes GPS. The location unit 351 also includes one or more of Bluetooth®, Wi-Fi®, NFC, RFID, UWB, and infrared. In some embodiments, the location unit 351 uses GPS to determine the current location while the user is outside, and one of the other location units 351 to determine a more specific location of the user while the user is inside. For example, the location unit 351 may use Wi-Fi® inside a shopping mall to determine which store a user is inside.

In some embodiments where the computing device 300 is a user device, the computing device 300 includes a display 353. The display 353 may connect to the I/O interface 339 to display content, e.g., a user interface, and to receive touch (or gesture) input from a user. The display 353 can include any suitable display device such as a liquid crystal display (LCD), light emitting diode (LED), or plasma display screen, television, monitor, touchscreen, or other visual display device.

The storage device 355 stores data related to the hearing application 103. For example, the storage device 355 may store hearing profiles generated by the hearing application 103, sets of test sounds, a hearing profile, training data for a machine-learning model, and one or more presets.

Although particular components of the computing device 300 are illustrated, other components may be added or removed.

Example Hearing Application 103

The hearing application 103 includes a user interface module 302, a hearing test module 304, a profile module 306, and a preset module 308. In some embodiments, one or more of the modules are part of a computing device 300 that is an auditory device and one or more of the modules are part of a computing device 300 that is a user device. For example, a first computing device 300 may be an auditory device that includes the hearing test module 304. A second computing device may be a user device that includes the user interface module 302, the hearing test module 304, the profile module 306, and the preset module 308.

The user interface module 302 generates graphical data for displaying a user interface. In some embodiments, a user downloads the hearing application 103 onto a computing device 300. The user interface module 302 may generate graphical data for displaying a user interface where the user provides input that the hearing test module 304, the profile module 306, and/or the preset module 308 uses to generate/ update a user profile for a user. For example, the user may provide a username and password, input their name, and provide an identification of an auditory device (e.g., identify whether the auditory device is a hearing aid, headphones, earbuds, or a speaker device).

In some embodiments, the user interface includes an option for specifying a particular type of auditory device and a particular model. For example, the hearing aids may be Sony C10 self-fitting over-the-counter hearing aids (model CRE-C10) or E10 self-fitting over-the-counter hearing aids (model CRE-E10). The identification of the type of auditory device is used for, among other things, determining a beginning decibel level for the test sounds. For example, because hearing aids, earbuds, and headphones are so close to the ear (and are possibly positioned inside the ear), the beginning decibel level for a hearing aid is 0 decibels. For testing of a speaker device, the speaker device should be placed a certain distance from the user and the beginning decibel level may be modified according to that distance. For example, for a speaker device that is within 5 inches of the user, the beginning decibel level may be 10 decibels.

In some embodiments, once the user has selected a type of auditory device, the user interface module 302 generates a user interface for specifying a model of the auditory device. For example, the user interface module 302 may generate graphical data for displaying a list of different types of Sony headphones. For example, the list may include WH-1000XM4 wireless Sony headphones, WH-CH710N wireless Sony headphones, MDR-ZX110 wired Sony headphones, etc. Other Sony headphones may be selected. In some embodiments, the user interface module 302 may generate graphical data to display a list of models from other manufacturers.

The user interface module 302 generates graphical data for displaying a user interface that includes an option for a user to take a hearing test. For example, the hearing test module 304 may implement pink noise band testing, speech testing, music testing, etc. In some embodiments, the user may select which type of test is performed first. In some embodiments, before testing begins, the user interface includes an instruction for the user to move to an indoor area that is quiet and relatively free of background noise.

Figure 4A:
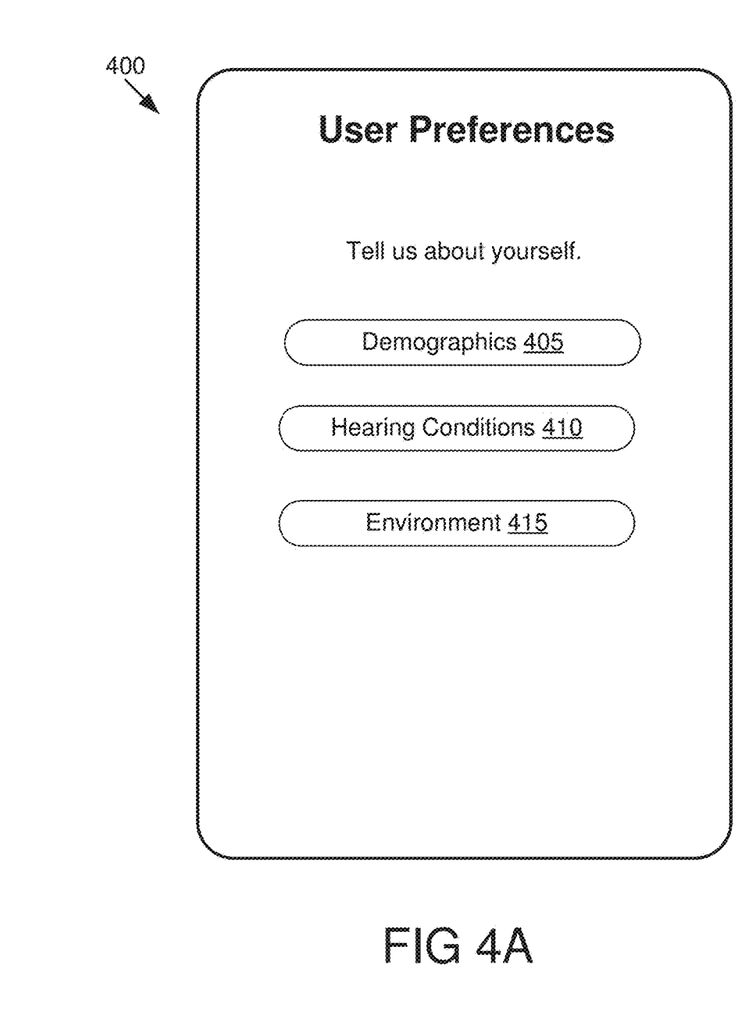
FIG. 4A is an example user interface for configuring user preferences according to some embodiments described herein.

In some embodiments, the user may reject the option to take the hearing test. The user interface module 302 generates graphical data that updates the user interface to include a list of user preferences. The user preferences may include questions about demographics, questions about hearing conditions, and environmental preferences. FIG. 4A is an example user interface 400 for configuring user preferences where the user interface 400 includes the option to select a demographics button 405, a hearing conditions button 410, and an environment button 415. Selecting any of the buttons may cause the user interface module 302 to generate graphical data for displaying a user interface with questions about the selected subject.

The questions about demographics may include questions about age, sex, location, etc. The questions about hearing conditions may include whether the user has experiences hearing loss, whether the user has any medical conditions that affect the user's hearing (e.g., tinnitus), and whether the user experiences trouble hearing in certain situations (e.g., restaurants, cars, etc.). The questions about environment may include if there are certain environments where the user wants hearing protection, such as if the user works at a construction site, goes to loud musical events, has trouble hearing in restaurants, etc. The user interface may include boxes next to subjects, fields to receive user input, radio buttons, etc. to receive information about user preferences.

In some embodiments, the profile module 306 and the preset module 308 use the answers to the user preferences to generate recommendations for a set of profiles and a set of presets, respectively. In some embodiments, the environment may also include questions about whether the user has particular hobbies that would benefit from a particular preset. For example, if the user frequently goes birding, the preset module 308 may recommend a birding preset that increases the gain for certain frequencies associated with bird calls.

In some embodiments, the user interface module 302 generates graphical data for displaying a user interface for selecting one or more profiles from a set of profiles and one or more presets from a set of presets. In some embodiments, the user interface module 302 generates graphical data for displaying a user interface for specifying parameters associated with a preset. For example, the user may specify a maximum preferred volume, a width of bands used for the parametric equalizer preset, etc. In one embodiment, the user interface module 302 generates graphical data for displaying a user interface that enables a user to specify an ambient noise condition for which the user wants to reduce or block the sound as is discussed in greater detail below with reference to FIG. 4D.

In some embodiments, the user interface module 302 generates graphical data for a user interface that includes icons for different presets that allows the user to modify the one or more presets. For example, the user interface may include an icon and associated text for a noise cancellation preset, an ambient noise preset, a factory noise preset, a baby noise preset, an airplane noise preset, a tool preset, a sports game preset, a work preset, a home preset, a concert preset, a traffic noise preset, a subway noise preset, a firetruck preset, a fire alarm preset, etc. The type of noise preset may include individual icons for presets corresponding to each type of noise, such as one for construction noise and another for noises at a particular frequency.

In some embodiments, the user interface module 302 generates graphical data for displaying a user interface that includes an option to override the one or more presets. For example, a user may switch presets because the user has moved from a previous location to a current location and the presets no longer apply. In some embodiments, the preset module 308 identifies that the user feedback of changing presets indicates that the distance threshold associated with the previous location should be modified to reflect the distance when the user changed the presets.

In some embodiments, after the user has used a selected profile, the user may request to take a hearing test to obtain a more precise hearing profile. As a result, the user interface module 302 generates graphical data for displaying a user interface to select a number of listening bands for the hearing testing. For example, the user interface may include radio buttons for selecting a particular number of listening bands or a field where the user may enter a number of listening bands.

Once the different tests begin, in some embodiments, the user interface module 302 generates graphical data for displaying a user interface with a way for the user to identify when the user hears a sound generated by the auditory device. For example, the user interface may include a button that the user can select when the user hears a sound. In some embodiments, the user interface module 302 generates a user interface during speech testing that includes a request to identify a particular word from a list of words. This helps identify words or sound combinations that the user may have difficulty hearing.

In some embodiments, the user interface module 302 may generate graphical data for displaying a user interface that allows a user to repeat the hearing tests. For example, the user may feel that the results are inaccurate and may want to test their hearing to see if there has been an instance of hearing loss that was not identified during testing. In another example, a user may experience a change to their hearing conditions that warrants a new test, such as a recent infection that may have caused additional hearing loss.

The hearing test module 304 conducts a hearing test by instructing the speaker 349 to emit sounds. In some embodiments, the hearing test is administered by a user marking in a user interface displayed on the user device whether the user heard a particular sound. In some embodiments, the hearing test module 304 stored on the user device generates the hearing profile once testing is complete and transmits the hearing profile to the user device.

The hearing test module 304 generates a hearing profile after receiving user input provided via the user interface. For example, the hearing test module 304 instructs the auditory device to play a sound at a particular decibel level, receives user input via the user interface when the user can hear the sound, and generates a hearing profile that indicates a frequency at which the user can hear the sound. The hearing test module 304 may use multiple types of tests. For example, the hearing test module 304 may implement pink band testing that determines the decibels at which pink bands are audible to users. The hearing test module 304 may also implement speech testing to determine circumstances when speech is most audible to the user and implement music testing to determine circumstances when music is most audible to the user.

In some embodiments, the hearing test module 304 transmits the hearing profile and any selected profiles to a server so that a hearing application 103 on the server may identify differences between the profiles that may be used to create future profiles. For example, if the profiles were generally similar for most frequencies, but there is a significant difference between the profiles for a certain frequency band, the feedback may be used to generate future profiles that are closer to the hearing profile generated for the user.

The profile module 306 receives one or more user preferences from the user. For example, the user may provide an age, sex, and medical condition. The profile module 306 selects profiles based on the user preferences. For example, the age and sex information may be used to select a demographic-based profile, such as a profile that is tailored for women over 60.

The medical condition may be used to select a hearing-condition based profile. For example, if a user has otosclerosis, which is an abnormal hardening of body tissue, the profile module 306 may apply an otosclerosis profile that amplifies certain sounds based on hearing aid resulting from the illness. Other examples include noise-induced hearing loss, Meniere's disease, auditory neuropathy, auditory processing disorder, ear infections from childhood, enlarged vestibular aqueducts and childhood hearing loss, Pendred syndrome, tinnitus, usher syndrome, vestibular schwannoma (acoustic neuroma), and neurofibromatosis.

In some embodiments, the profile module 306 may select one or more popular profiles to include in the set of profiles. The popular profiles may be based on a combination of user ratings, user downloads, limited to a particular region or demographic, etc.

In some embodiments, the profile module 306 may select an audiologist-designed profile. The audiologist-designed profile may be further based on additional information, such as demographic information or based on a particular complaint provided by the user (e.g., trouble hearing in restaurants).

In some embodiments, the profile module 306 uses a machine-learning model to output a machine-learning profile. The machine-learning model may be trained using training data that includes different user preferences and corresponding hearing profiles. In some embodiments, the hearing profiles may be generated by an audiologist. In some embodiments, the hearing profiles may also include hearing profiles generated from hearing tests, such as a hearing test administered by the hearing test module 304. The training data may be labelled with one or more hearing profiles.

The machine-learning model receives training data that includes user preferences as input to the machine-learning model and outputs one or more training profiles that correspond to the user preferences. The profile module 306 compares the one or more machine-learning profiles to ground truth data that describes the appropriate hearing profiles for the user preferences. The profile module 306 calculates a loss function that reflects the difference between the one or more training profiles and the ground truth data. The profile module 306 modifies the parameters of the machine-learning model based on the loss function. The profile module 306 continues this process iteratively until the machine-learning model consistently outputs one or more profiles with a minimal loss value.

In some embodiments, the machine-learning model is a neural network. Neural networks can learn and model the relationships between input data and output data that are nonlinear and complex. The neural network may include an input layer, a hidden layer, and an output layer. The input layer may receive input data, the hidden layer takes its input from the input layer or other hidden layers, and the output layer provides the final result of the data processing. The neural network may use a backpropagation algorithm that learns continuously by using corrective feedback loops to improve predictive analytics. The neural network may be a convolutional neural network where the hidden layers perform specific mathematical functions, such as summarizing or filtering.

In some embodiments, the trained machine-learning model receives user preferences as input and the machine-learning model outputs a machine-learning profile. In some embodiments, the profile module 306 provides the user preferences to a server, which includes a machine-learning model that provides the machine-learning model to the computing device 300. In some embodiments, in response to the user rejecting an option to take a hearing test, the profile module 306 instructs the auditory device to implement the machine-learning profile.

Figure 4B:
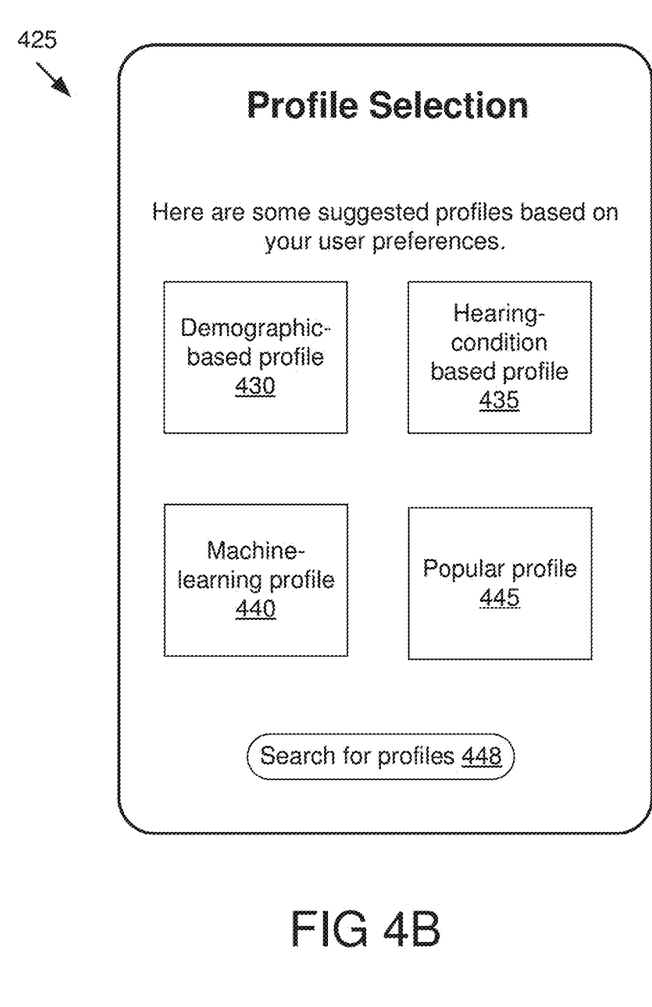
FIG. 4B is an example user interface of a set of profiles that are suggested based on user preferences according to some embodiments described herein.

The profile module 306 instructs the user interface module 302 to update the user interface to include a set of profiles based on the user preferences. FIG. 4B is an example user interface 425 of a set of profiles that are suggested based on user preferences. In this example, the set of profiles includes a demographic-based profile 430, a hearing-condition based profile 435, a machine-learning profile 440, and a popular profile 445.

In some embodiments, a user may select multiple profiles from the set of profiles. The profile module 306 may combine the features from multiple profiles by summing the different profiles. For example, the profile module 306 may combine a demographic-based profile 430 that addresses hearing loss in older men and a hearing-condition based profile 435 that addresses hearing difficulties due to tinnitus. In another example, the profile module 306 may combine a profile for a person that uses a profile for high-frequency hearing loss and a profile used when a person is birdwatching. Summing the two profiles results in the person getting the benefits of both profiles at once.

Once a user selects a profile from the set of profiles, the profile module 306 instructs an auditory device to implement the selected profile. In some embodiments, the auditory device saves the selected profile and applies it in future use.

Figure 4C:
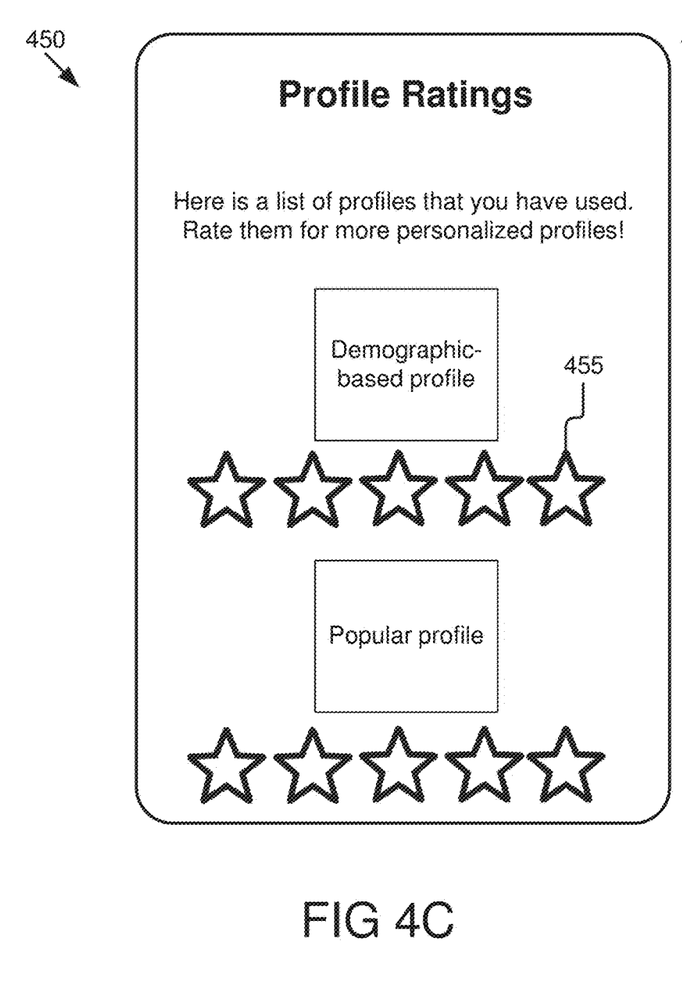
FIG. 4C is an example user interface for rating profiles according to some embodiments described herein.

In some embodiments, the profile module 306 scores selected profiles. The profile module 306 may receive a rating from the user and score the selected profile based on the rating from the user. FIG. 4C is an example user interface 450 for rating profiles. In this example, the user has used a demographic-based profile and a popular profile. The user may select between one and five stars. Other types of ratings may be used, such as using a drop-down box, entering a value into a field, etc.

The profile module 306 may use additional information to score selected profiles. For example, the profile module 306 may score selected profiles based on frequency of use. The profile module 306 may use the ratings to update popular profiles based on the score associated with the selected profile. For example, if the score for a popular profile falls below a score associated with a different profile, the updated rating results in the different profile being displayed before the popular profile.

In some embodiments, a preset module 308 generates a set of presets for a user. The set of presets may be based on user preferences as well. The set of presets may be selected manually when a user selects a preset from a set of presets on a user interface, by providing verbal instructions that are detected by a microphone 341 or a voice pick-up sensor (not illustrated), providing physical instructions by pressing a button on the auditory device or making a gesture that is detected by a motion sensor, etc.

In some embodiments, the preset module 308 applies a preset based on other factors, such as based on using the location unit 351 to determine a current location of the computing device 300 and activating a preset based on the current location. In some embodiments, the preset module 308 receives the current location via the I/O interface 339 from the location unit 351. The location unit 351 may include GPS that identifies the current location. In some embodiments, where a more precise location is needed, the location unit 351 provides the current location using at least one of Bluetooth®, Wi-Fi®, NFC, RFID, ultra-wideband, or infrared. In some embodiments, the location unit 351 provides a first current location using GPS and a second current location using one or more of the other methods. For example, the location unit 351 may first use GPS to provide an approximate location and then one of the other methods to provide the more precise methods. In another example, the location unit 351 may use GPS to provide the first current location and then, responsive to detecting that the user moved inside, provides the second current location using one of the other methods.

In some embodiments, the preset module 308 applies a preset based on detecting an ambient noise condition, such as when a user goes to a loud concert and the preset provides hearing protection by reducing or blocking noises above a particular threshold.

In some embodiments, the preset module 308 determines whether one or more presets have previously been used in the current location by a user. For example, the one or more presets may be associated with GPS coordinates, particular buildings, etc. If the one or more presets have been previously used in the current location by the user, the preset module 308 applies the one or more presets. For example, if the preset module 308 is part of the auditory device, the preset module 308 instructs the speaker 349 to apply the one or more presets. If the preset module 308 is part of the user device, the preset module 308 transmits instructions to the auditory device to apply the one or more presets.

The one or more presets predict when to reduce, remove, and/or amplify sounds at particular frequencies based on patterns associated with the ambient noise condition. For example, the sound of a baby may adhere to a particular pattern where the baby's cry is painfully loud at first, but then decreases, and then increases again. The preset module 308 may apply a high-frequency shelf to block the high frequencies and a parametric equalizer preset to reduce the loudness of the scream. In another example, a band saw may emit sounds at particular decibel levels and particular frequencies in a pattern that the preset module 308 uses to determine when to reduce, remove, and/or amplify sounds.

If the one or more presets have not previously been used, the preset module 308 may instruct the user interface module 302 to generate graphical data for displaying a list of suggested presets that correspond to the current location. In some embodiments, the suggested presets are based on presets generated for other users where the users have consented to their information being anonymized. For example, as discussed below, the preset module 308 may generate one or more presets using a machine-learning model. The preset module 308 may instruct the user interface to provide the most popular presets as suggested options for the user. The set of presets may include a ranked set of the most popular presets selected by users generally, the most popular presets selected by users that are similar to the user, an alphabetic list of presets, etc.

In some embodiments, the suggested presets are based on defaults generated for the current location based on various ambient noise conditions. For example, the preset module 308 may generate default presets for types of locations, such as grocery stores, daycare, school, a racetrack, sports venues, concert venues, areas with large amounts of traffic, a work building where background noise is suppressed and voices are enhanced, etc.

The user may select one or more suggested presets from the list of suggested presets that correspond to the current location. The preset module 308 applies the one or more suggested presets. For example, if the preset module 308 is on the user device, the preset module 308 transmits instructions to the auditory device about how to apply the one or more suggested presets that were selected.

If the preset module 308 is on the auditory device, the preset module 308 may instruct the speaker to apply the one or more presets. For example, the preset module 308 may determine that the ambient noise condition includes one or more frequencies that exceed a threshold frequency and the preset module 308 may apply a preset that includes reducing or blocking the ambient noise condition corresponding to the one or more frequencies. The preset module 308 may instruct the filter block 352 to apply a filter that reduces or blocks the one or more frequencies.

In some embodiments, the one or more presets include an adaptive noise cancellation preset. The preset module 308 may apply the preset by instructing the digital signal processor 345 to reduce or block the ambient noise condition using adaptive noise cancellation by mapping the ambient noise condition to what the user will hear with the auditory device in order to generate an anti-noise signal that is an inverted waveform that effectively cancels the waveform corresponding to the ambient noise condition.

In some embodiments, the one or more presets includes a noise cancellation and ambient noise preset that may cause the auditory device to provide a user with cancellation of noises that are not directly surrounding the user while allowing in sounds that directly surround the user through the ambient noise aspect of the preset. In some examples, the noise cancellation and ambient noise preset includes three options: a first setting activates the ambient noise function and the noise cancellation function, a second setting turns off the noise-cancellation function so only the ambient noise function is active, and a third setting turns off the ambient noise function so only the noise cancellation function is activated.

In some embodiments, the preset module 308 may apply a preset that adjusts the gain of sound at a particular frequency. For example, the preset module 308 may instruct the compressor 354 to adjust the gain of the background noise associated with a person that is whispering while other presets reduce sounds, such as from a basketball game that includes reflective noise that interferes with a user's ability to hear. The compressor 354 may adjust the frequencies at a first predetermined time (e.g., 10 ms, 1 second) and stop adjusting the frequencies at a second predetermined time (e.g., 5 ms, 2 seconds). The timing for applying and stopping the compressor 354 may be referred to as attack time and release time, respectively.

The preset module 308 may apply one or more presets that include different factors based on a frequency associated with ambient noise condition. For example, the preset module 308 may apply active noise cancellation, automatic gain control, a high-frequency shelf, and/or a parametric equalizer based on a threshold. Above an amplitude threshold, the preset module 308 may apply active noise cancellation. For example, the preset module 308 may apply active noise cancellation for any sounds with an amplitude above a threshold based on determining that the background noise is associated with an ambient condition. In some embodiments, the preset module 308 may apply other presets when the ambient noise condition is associated with a frequency or amplitude that exceeds the threshold. For example, the preset module 308 may apply one or more of a high-frequency (HF) shelf, a parametric equalizer (PEQ), and gain to frequencies that exceed the threshold.

The preset module 308 may apply gain as a function of a frequency of the ambient noise condition. For example, the preset module 308 may instruct the amplifier 356 to increase the gain of frequencies where the hearing profile associated with a user indicates that the user has suffered hearing loss as long as the gain is below a threshold protection line. In some embodiments, the gain may be associated with the threshold such that gain control is applied to all frequencies below a threshold or all frequencies above the threshold. The preset module 308 may apply a high-frequency shelf preset by instructing the digital signal processor 345 to reduce a sound level associated with a particular frequency so that it does not exceed a threshold protection.

The preset module 308 may apply a parametric equalizer preset by applying a gain for one or more frequency bands. In some embodiments, the preset module 308 may determine, or the user may define, one or more of a width of the one or more frequency bands, a center frequency for each of the one or more frequency bands, a quality factor (Q) of the one or more frequency bands that is a measure of a sharpness of a resonant peak, and a gain for each of the one or more frequency bands.

In some embodiments, the parametric equalizer may also be used by the preset module 308 to define a notch that reduces or blocks the background noise of an ambient noise condition for a particular frequency. For example, a user may have defined an unpleasant noise at a particular frequency that the user wants to be blocked out. For example, the user may have selected a preset that blocks out the noise of tonal machinery noise. As a result, the preset module 308 applies a parametric equalizer presetting that includes a notch preset curve to block out the frequency associated with tonal machinery noise.

The music preset may include a variety of different user preferences relating to music. For example, the user preferences may include an identification that there are certain frequencies or situations during which the user experiences hypersensitivity. For example, the user may identify a particular frequency that causes distress, a particular action that bothers a user (such as construction noises), or based on a particular condition like misophonia (such as chewing or sniffing noises).

In some embodiments, the preset module 308 generates a new preset for a current location using a machine-learning model. The machine-learning model may be trained using training data that includes different ambient noise conditions and information about how the different ambient noise conditions change as a function of time. For example, when a firework is launched the whistling noise is between 160 to 200 Hertz and the explosion is 16-25 Hertz. There is a predictable pattern for how long it takes for the firework to whistle and then explode. In another example, at a soccer game when a player scores a goal, the cheering follows a pattern of noise that becomes rapidly loud and then quickly attenuates. In yet another example, construction noise may function in a predictable pattern as identified by a machine-learning model.

In some embodiments, the training data also includes a set of presets that reduce or block the background noise associated with the different ambient noise conditions. The set of presets may be labelled for the types of ambient noise conditions and function as part of a supervised learning process for training the machine-learning model.

The preset module 308 generates feature embeddings from the training data that group features of the different noise conditions based on similarity. The machine-learning model is trained to recognize patterns in different ambient conditions such that the machine-learning model will be able to predict how different ambient conditions will behave in the future based on the patterns.

The machine-learning model receives training data that includes ambient noise conditions as input to the machine-learning model and outputs one or more training presets that correspond to each training ambient noise condition. The preset module 308 compares the one or more training presets to ground truth data that describes the appropriate presets for the ambient noise condition. The preset module 308 calculates a loss function that reflects the difference between the one or more training presets and the ground truth data. The preset module 308 modifies the parameters of the machine-learning model based on the loss function. The preset module 308 continues this process iteratively until the machine-learning model consistently outputs one or more presets with a minimal loss value.

In some embodiments, the machine-learning model is a neural network.

In some embodiments, the machine-learning model may be used to generate one or more presets. The preset module 308 includes a machine-learning model that receives information about the background noise as inputs along with the one or more presets and outputs a determination that one or more presets correspond to the ambient noise condition. The training data may be labelled with one or more presets corresponding to users with different demographics (e.g., sex, age, auditory conditions, etc.). The preset module 308 may train the machine-learning model using supervised training data to receive background noise associated with an ambient noise condition as input and output the one or more presets.

In some embodiments, one or more of the presets in the set of presets are generated by a machine-learning model where the machine-learning model outputs the presets independently and/or the machine-learning model outputs the presets based on input from a user. For example, a user may select a button on a user interface to record a sample for a period of time of the ambient noise condition that the user wants reduced or blocked and the sample is used as input to the machine-learning model. The recording may be performed for a predetermined amount of time, identified by the user as starting and stopping, etc. The machine-learning model may output one or more presets for the ambient noise condition that modify adjustments in sound levels based on the patterns associated with the ambient noise condition.

Figure 4D:
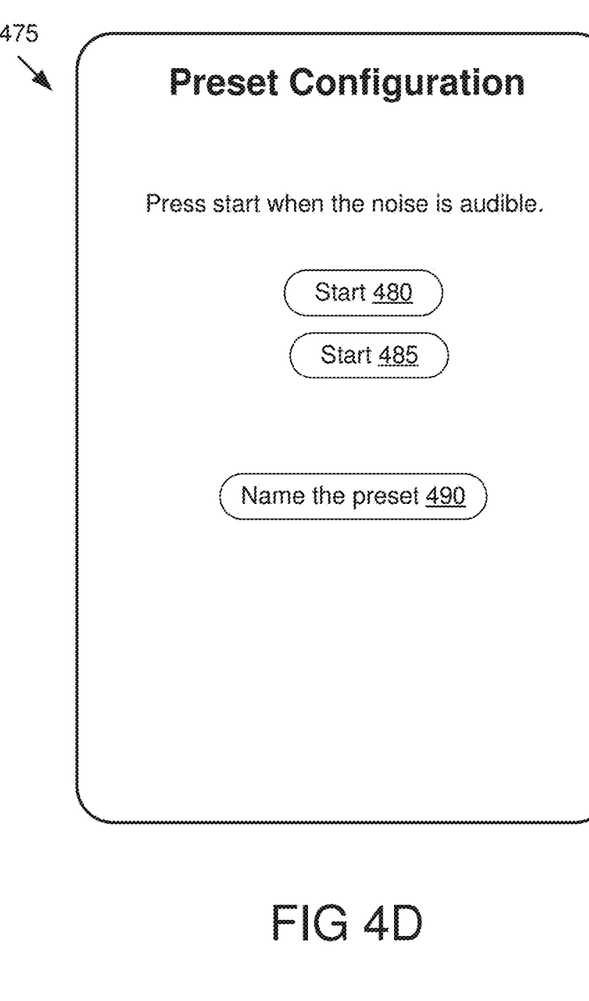
FIG. 4D is an example user interface for using a machine-learning model to output a profile according to some embodiments described herein.

FIG. 4D is an example user interface 475 of an option for configuring a preset. In this example, the user is instructed to press the start button 480 when an ambient condition that the user wants to reduce or block is audible. In some embodiments, the user device records a sample for a predetermined amount of time. In some embodiments, the user interface 475 includes a stop button 485 that the user selects to end the recording. The user interface 475 also includes a button 490 for naming the preset. Once the preset is created, the preset module 308 associates the preset with the current location and applies the preset in the future when the user is at or near the current location.

In some embodiments, the preset module 308 receives feedback from a user. The user may provide user input to a user interface that changes one or more presets. For example, the user may change a preset for streaming audio to include noise cancellation. The preset module 308 updates the one or more presets based on the feedback. In some embodiments, the preset module 308 does not change the one or more presets until a threshold amount of feedback has been received. For example, the preset module 308 may not change a preset until the user has changed the preset a threshold of four times (or three, five, etc.).

In some embodiments, the user may provide user input for changing the presets using hardware that is part of the auditory device or the user device. For example, the user may provide a voice command that is detected by the microphone 341, a voice pick-up sensor (not illustrated) that identifies words or vibrations caused by a user speaking that instructs the auditory device to turn on or off one or more of the presets. In another example, the user may make a gesture that is detected by a motion sensor (not illustrated) that determines that the user is instructing one or more presets to be turned on or off. The preset module 308 may determine that the user input is feedback for modifying the machine-learning model if the user changes the settings more than a predetermined amount of time.

Example Methods

Figure 5:
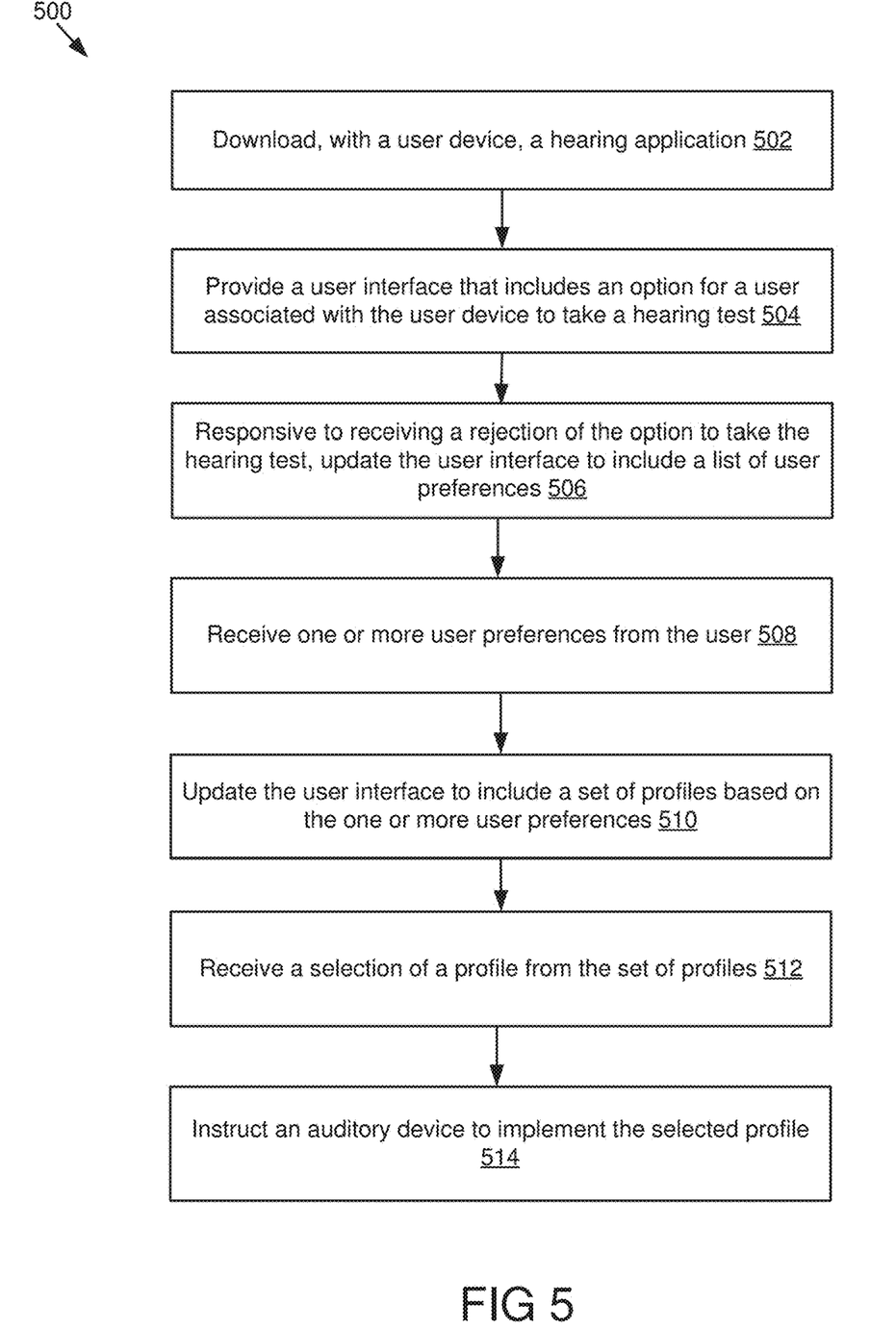
FIG. 5 illustrates a flowchart of an example method to provide a set of customized profiles according to some embodiments described herein.

FIG. 5 illustrates a flowchart of an example method 500 to provide a set of customized profiles. The method 500 may be implemented by a hearing application that is stored on a user device or in part a user device and in part an auditory device.

The method 500 may start with block 502. At block 502, a user device downloads a hearing application. Block 502 may be followed by block 504.

At block 504, a user interface is provided that includes an option for a user associated with the user device to take a hearing test. For example, the hearing test may include pink-band testing, music testing, or speech testing. Block 504 may be followed by block 506.

At block 506, responsive to receiving a rejection of the option to take the hearing test, update the user interface to include a list of user preferences. For example, the user preferences may be divided into demographic information, hearing conditions, and environmental preferences. Block 506 may be followed by block 508.

At block 508, one or more user preferences are received from the user. Block 508 may be followed by block 510.

At block 510, the user interface is updated to include a set of profiles based on the one or more user preferences. For example, the set of profiles may include a demographic-based profile, a hearing-condition based profile, a machine-learning profile, and a popular profile. Block 510 may be followed by block 512.

At block 512, a selection of a profile from the set of profiles is received. Block 512 may be followed by block 514.

At block 514, an auditory device is instructed to implement the selected profile.

Figure 6:
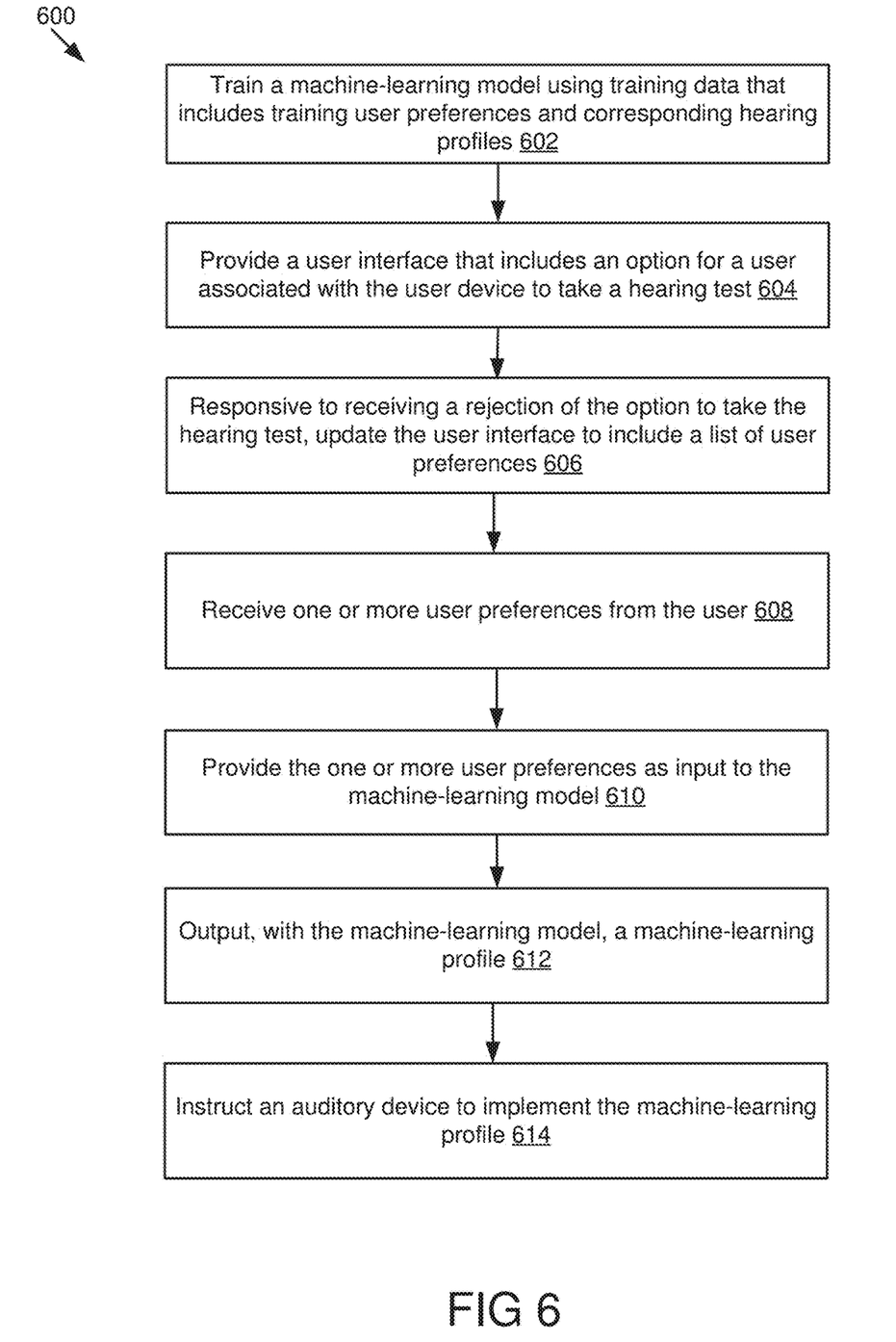
FIG. 6 illustrates a flowchart of an example method to generate a profile using a machine-learning model according to some embodiments described herein.

FIG. 6 illustrates a flowchart of an example method to generate a profile using a machine-learning model. The method 600 may be implemented by a hearing application that is stored on a user device or a combination of a server, a user device, and/ort an auditory device.

The method 600 may begin with block 602. At block 602, a machine-learning model is trained using training data that includes training user preferences and corresponding hearing profiles. In some embodiments, the machine-learning model is trained on the server to take advantage of higher processing power. Block 602 may be followed by block 604.

At block 604, a user interface that includes an option for a user associated with the user device to take a hearing test is provided. Block 604 may be followed by block 606.

At block 606, responsive to receiving a rejection of the option to take the hearing date, the user interface is updated to include a list of user preferences. Block 606 may be followed by block 608.

At block 608, one or more user preferences are received from the user. Block 608 may be followed by block 610.

At block 610, the one or more user preferences are provided as input to the machine-learning model. Block 610 may be followed by block 612.

At block 612, the machine-learning model outputs a machine-learning profile. Block 612 may be followed by block 614.

At block 614, an auditory device is instructed to implement the machine-learning profile. In some embodiments, if the user is unhappy with the machine-learning profile, the hearing application updates the user interface to provide a list of profiles based on the user preferences.

Although the description has been described with respect to particular embodiments thereof, these particular embodiments are merely illustrative, and not restrictive.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

A "processor" includes any suitable hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems. Examples of processing systems can include servers, clients, end user devices, routers, switches, networked storage, etc. A computer may be any processor in communication with a memory. The memory may be any suitable processor-readable storage medium, such as random-access memory (RAM), read-only memory (ROM), magnetic or optical disk, or other non-transitory media suitable for storing instructions for execution by the processor.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A computer-implemented method comprising:
   downloading, with a user device, a hearing application;
   providing a user interface that includes an option for a user associated with the user device to take a hearing test;
   responsive to receiving a rejection of the option to take the hearing test, updating the user interface to include a list of user preferences;
   receiving one or more user preferences from the user;
   updating the user interface to include a set of profiles based on the one or more user preferences;
   receiving a selection of a profile from the set of profiles; and
   instructing an auditory device to implement the selected profile.

2. The method of claim 1, wherein the user preferences include an identification of demographic information for the user and the set of profiles includes a demographic-based profile.

3. The method of claim 1, wherein the user preferences include an identification of a hearing condition and the set of profiles includes a hearing-condition based profile.

4. The method of claim 1, wherein the set of profiles includes one or more popular profiles.

5. The method of claim 4, further comprising:
   providing an option to rate the selected profile;
   scoring the selected profile based on a rating from the user; and
   updating the one or more popular profiles based on the score associated with the selected profile.

6. The method of claim 1, wherein the set of profiles includes an audiologist-designed profile.

7. The method of claim 1, further comprising:
   providing user preferences as input to a machine-learning model; and
   outputting, with the machine-learning model, a machine-learning profile.

8. The method of claim 1, further comprising:
   updating the user interface to include a set of presets.

9. The method of claim 8, further comprising:
   receiving a selection of the option to create a new preset for a current location;
   sampling a background noise for a period of time; and
   outputting, with a machine-learning model, the new preset for an ambient noise condition that modifies adjustments in sound levels based on patterns associated with the ambient noise condition.

10. A user device comprising:
    one or more processors; and logic encoded in one or more non-transitory media for execution by the one or more processors and when executed are operable to:

receive a trained machine-learning model;

provide a user interface that includes an option for a user associated with the user device to take a hearing test;

responsive to receiving a rejection of the option to take the hearing test, update the user interface to include a list of user preferences;

receive one or more user preferences from the user;

provide the one or more user preferences as input to the trained machine-learning model;

output, with the trained machine-learning model, a machine-learning profile; and instruct an auditory device to implement the machine-learning profile.

11. The user device of claim 10, wherein the logic is further operable to:

update the user interface to include a set of profiles based on the one or more user preferences;

receive a selection of a profile from the set of profiles; and instruct an auditory device to implement the selected profile.

12. The user device of claim 11, wherein the user preferences include an identification of a hearing condition and the set of profiles includes a hearing-condition based profile.

13. The user device of claim 11, wherein the user preferences include an identification of a hearing condition and the set of profiles includes a hearing-condition based profile.

14. The user device of claim 11, wherein the set of profiles includes one or more popular profiles.

15. The user device of claim 14, wherein the logic is further operable to:

provide an option to rate the selected profile;

score the selected profile based on a rating from the user; and update the one or more popular profiles based on the score associated with the selected profile.

16. Software encoded in one or more computer-readable media for execution by one or more processors of a device and when executed is operable to:

download, with a user device, a hearing application;

provide a user interface that includes an option for a user associated with the user device to take a hearing test;

responsive to receiving a rejection of the option to take the hearing test, update the user interface to include a list of user preferences;

receive one or more user preferences from the user;

update the user interface to include a set of profiles based on the one or more user preferences;

receive a selection of a profile from the set of profiles; and instruct an auditory device to implement the selected profile.

17. The software of claim 16, wherein the user preferences include an identification of demographic information for the user and the set of profiles includes a demographic-based profile.

18. The software of claim 16, wherein the user preferences include an identification of a hearing condition and the set of profiles includes a hearing-condition based profile.

19. The software of claim 16, wherein the set of profiles includes one or more popular profiles.

20. The software of claim 19, wherein the software is further operable to:

provide an option to rate the selected profile;

score the selected profile based on a rating from the user; and update the one or more popular profiles based on the score associated with the selected profile.

* * * * *